Figure 1:
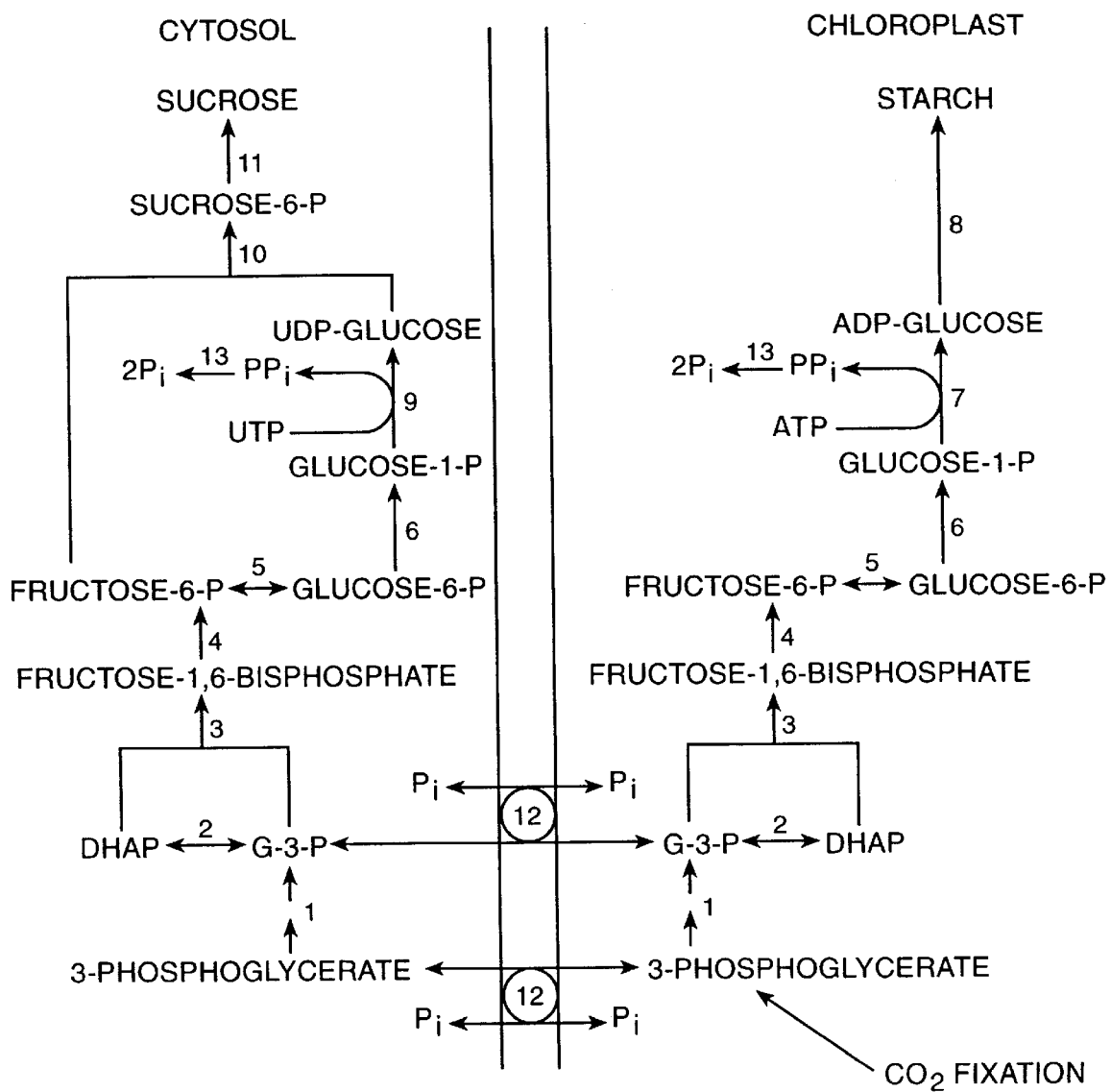

United States Patent [19]

Keeling et al.

[11] Patent Number: 5,824,790
[45] Date of Patent: Oct. 20, 1998

[54] MODIFICATION OF STARCH SYNTHESIS IN PLANTS

[75] Inventors: Peter Lewis Keeling, Ames, Iowa; Mary E. Knight, Crowthorne, England; Hanping Guan, Ames, Iowa

[73] Assignee: Zeneca Limited, London, England

[21] Appl. No.: 572,951

[22] Filed: Dec. 15, 1995

Related U.S. Application Data

[63] Continuation-in-part of Ser. No. 346,602, Nov. 29, 1994, which is a continuation-in-part of Ser. No. 263,921, Jun. 21, 1994, abandoned.

[51] Int. Cl.$^6$ ............... C12N 15/05; C12N 15/29; C07H 21/04; A01H 5/00
[52] U.S. Cl. ............. 536/23.6; 800/205; 435/172.3; 435/172.1; 935/67; 935/64
[58] Field of Search ............... 800/205; 435/172.3, 435/172.1; 47/58, DIG. 4; 536/24.1, 23.6; 935/67, 52, 55, 64

[56] References Cited

U.S. PATENT DOCUMENTS 5,034,323  7/1991  Jorgensen et al. ............. 435/172.3
5,453,566  9/1995  Shewmaker et al. ............ 800/205

OTHER PUBLICATIONS

Baba et al. Plant Physiology vol. 103 pp. 565–573 1993.
Van der Krol The plant Cell vol. 2. p. 291 1990.
Van der Krol Plant Molecular biology vol. 14. p. 457 1990.

*Primary Examiner*—Gary Benzion
*Attorney, Agent, or Firm*—Cushman Darby & Cushman IP Group of Pillsbury Madison & Sutro LLP

[57] ABSTRACT

A method of producing a plant with novel starch-synthesising ability comprises stably incorporating into the genome of a recipient plant at least one target gene encoding an enzyme involved in a starch or glycogen biosynthetic pathway. A plant with novel starch-synthesising ability may have novel starch quality (eg altered fine structure). Starch or glycogen biosynthetic enzymes include soluble starch synthase, branching enzyme, glycogen synthase, ADP-glucose pyrophosphorylase, self-glucosylating protein, glycogenin and amylogenin. Mutants involving said enzymes for use in this method are described, including specific gene-dosage combinations which provide novel starch fine structures and starch properties. DNA constructs for use in this method are described, as well as plants transformed with said DNA constructs, the seeds and progeny of such plants, and hybrids whose pedigree includes such plants.

6 Claims, 2 Drawing Sheets

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 2990 base pairs
( B ) TYPE: nucleic acid
( C ) STRANDEDNESS: both
( D ) TOPOLOGY: linear ( i i ) MOLECULE TYPE: cDNA ( x i ) SEQUENCE DESCRIPTION: SEQ ID NO:1:

```
GAATTCGCGG  CCGCCTTATT  TCTGGTTGGC  CACATACATC  ATCCAAAAAA  CTTTATTATT    60
GAATTACAAC  TAATAAGCAA  TCTAAAAGAG  GGCACCACCA  ATGATGTGTT  GTTGGTAGGA   120
GGCCGCTGGG  TCTGTCAAAG  CAAGTTGGAC  AAAGGGCAAC  AATTGTTGTA  GTTGTAAGAG   180
GGTTGCGGGG  TTAGCCGCAA  ACTGCTGGTA  GAAAGGCAGC  AACTGTTGCT  GTGTCAAGAA   240
GGAAGCACGG  TTTGCTGCAG  CTGTTGTGCC  CTGATGGTTT  GTACCAATGA  CTGCACCAAA   300
GATAGGGCTG  GCGATTGTTG  AAACAACAAG  GGCGATAAAG  GTATGTTGCT  TGCTGCGATT   360
GCTTGTTGAA  GCCTATATGG  TTGAAGAGCT  GGGTTTTCAC  ATATTGAAGC  TATAATTGAT   420
GGAAGGTATG  GGGGAAGAAG  GGAAGCTATA  GGAGCTTGTG  AGCATTGAGG  GAAAATTGTC   480
GCGTTAGCAA  CACATGTAGA  AAGAGCAAGG  AGCATAAGGA  GGGAAAATAT  CTTGGTCGCC   540
ATTGTTGCGC  GCGATCCACG  GCCCCCCCCC  CCCGCGCTCC  TGTCTGCTCT  CCCTCTCCGC   600
AATGGCGACG  CCCTCGGCCG  TGGGCGCCGC  GTGCCTCCTC  CTCGCGCGGG  CGCCTGGCCG   660
GCCGCCGTCG  GCGACCGGGC  GCGCCCGCGG  AGGCTCCAGC  GCGTGCTGCG  CCGCCGGTGC   720
GTCGCGGAGC  TGAGCAGGGA  GGGGCCCGCG  CCGCGCCCGC  TGCCACCCGC  GCTGCTGGCG   780
CCCCCGCTCG  TGCCCGGCTT  CCTCGCGCCG  CCGGCCGAGC  CCACGGGTGA  GCCGGCATCG   840
ACGCCGCCGC  CCGTGCCCGA  CGCCGGCCTG  GGGACCTCG   GTCTCGAACC  TGAAGGGATT   900
GCTGAAGGTT  CCATCGATAA  CACAGTAGTT  GTGGCAAGTG  AGCAAGATTC  TGAGATTGTG   960
GTTGGAAAGG  AGCAAGCTCG  AGCTAAAGTA  ACACAAAGCA  TTGTCTTTGT  AACCGGCGAA  1020
```

```
GCTTCTCCTT  AATCGAAAGT  CTGGGGGTCT  AGGAGATGTT  TGTGGTTCAT  TGCCAGTTGC      1080

TCTTGCTGCT  CGCGGTCACC  GTGTGATGGT  TGTAATGCCC  AGACATTTAA  ATGGTACCTC      1140

CGATAAGAAT  TATGCAAATG  CATTTTACTC  AGAAAAACAC  ATTCGGATTC  CATTCTTTGG      1200

CGGTGAACAT  GAAGTTACCT  TCTTCCATGA  GTATAGAGAT  TCAGTTGACT  GGGTGTTTGT      1260

TGATCATCCC  TCATATCACA  GACCTGGAAA  TTTATATGGA  GATAAGTTTG  GTGCTTTTGG      1320

TGATAATCAG  TTCAGATACA  CACTCCTTTG  CTATGCTGCA  TGTGAGGCTC  CTTTGGTCCT      1380

TGAATTGGGA  GGATATATTT  ATGGACAGAA  TTGCATGTTG  GTTGTCAATG  ATTGGCATGC      1440

CAGTCTAGAG  CCAGTCCTTC  TTGCTGCAAA  ATATAGACCA  TATGGTGTTT  ATAAAGACTC      1500

CCGCAGCATT  CTTGTAATAC  ATAATTTAGC  ACATCAGGGT  GTAGAGCCTG  CAAGCACATA      1560

TCCTGACCTT  GGGTTGCCAC  CTGAATGGTA  TGGAGCTCTG  GAGTGGGTAT  TCCCTGAATG      1620

GGCGAGGAGG  CATGCCCTTG  ACAAGGGTGA  GGCAGTTAAT  TTTTGAAAG   GTGCAGTTGT      1680

GACAGCAGAT  CGAATCGTGA  CTGTCAGTAA  GGGTTATTCA  TGGGAGGTCA  CAACTGCTGA      1740

AGGTGGACAG  GGCCTCAATG  AGCTCTTAAG  CTCCAGAAAG  AGTGTATTAA  ACGGAATTGT      1800

AAATGGAATT  GACATTAATG  ATTGGAACCC  TGCCACAGAC  AAATGTATCC  CCTGTCATTA      1860

TTCTGTTGAT  GACCTCTCTT  GAAAGGCTAA  ATGTAAGGT   GCATTGCAGA  AGGAGCTGGG      1920

TTTACCTATA  AGGCCTGATG  TTCCTCTGAT  TGGCTTTATT  GGAAGATTGG  ATTATCAGAA      1980

AGGCATTGAT  CTCATTCAAC  TTATCATACC  AGATCTCATG  CGGAAGAATG  TTCAATTTGT      2040

CATGCTTGGA  TCTGGTGACC  CAGAGCTTGA  AGATTGGATG  AGATCTACAG  AGTCGATCTT      2100

CAAGGATAAA  TTTCGTGGAT  GGGTTGGATT  TAGTGTTCCA  GTTTCCCACC  GAATAACTGC      2160

GGCTGGCGAT  ATATTGTTAA  TGCCATCCAG  ATTCGAACCT  TGTGGTCTCA  ATCAGCTATA      2220

TGCTATGCAG  TATGGCACAG  TTCCTGTTGT  CCATGCAACT  GGGGGCCTTA  GAGATACCGT      2280

GGAGAACTTC  AACCCTTTCG  GTGAGAATGG  AGAGCAGGGT  ACAGGGTGGG  CATTCGCACC      2340

CCTAACCACA  GAAAACATGT  TTGTGGACAT  TGCGAACTGC  AATATCTACA  TACAGGGAAC      2400

ACAAGTAATA  ATGGGAAGGG  CTAATGAAGC  CAGGCATGTC  AAAAGAGTTC  ACGTGGGACC      2460

ATGCCGCTGA  ACAATACGAA  CAAATCTTCC  AGTGGGCCTT  CATCGGATCG  ACCCGATGTT      2520

CAATGGAAAA  AAGGGACCAA  AGTTGGTTGG  TTCCTTGAAG  ATTATCAGTT  CATCATCCTA      2580

TAGTAAGCTG  AATGATGAAA  GAAAACCCCT  GTACATTACA  TGGAAGGCAG  ACCGGCTATT      2640

GGCTCCATTG  CTCCAATGTC  TGCTTTGGCT  GCCTTGCCTC  GATGGACCGG  ATGCAGTGAG      2700

GAATCCAGCG  AACGACAGTT  TTGAAGGATA  GGAAGGGGAG  CTGGAAGCAG  TCACGCAGGC      2760

AGGCAAGCCT  TCGCCGTTAA  TTCATATGGA  ACAAGCTGGA  GTCAGTTTCT  GCTGTGCCAC      2820

TCACTGTTTA  CCTTAAGATT  ATTACCTGTG  TTGTTCTCCT  TTGCTCGTTA  GGGCTGATAA      2880

CATAATGACT  CATTAAGAAT  ATAATTCACT  CTGCCTCGTT  TTTAATCTTA  AGTGAAGTCG      2940

AGATCTACTT  CGTCATTCCT  TCCCCGTTTA  AAAAAAAAAA  AAAAAAAAA                   2990
```

( 2 ) INFORMATION FOR SEQ ID NO:2:

( i ) SEQUENCE CHARACTERISTICS:
        ( A ) LENGTH: 2085 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:2:

```
AACGCCGCAT  TGGCACGTTG  AGATCAAGTC  CATCGTCGCC  GCGCCGCCGA  CGAGCATAGT        60
```

-continued

```
GAAGTTCCCA GGGCGCGGGC TACAGGATGA TCCTTCCCTC TGGGACATAG CGCCGGAGAC     120
TGTCCTCCCA GCCCCGAAGC CACTGCATGA ATCGCCTGCG GTTGACGGAG ATTCAAATGG     180
AATTGCACCT CCTACAGTTG AGCCATTAGT ACAGGAGGCC ACTTGGGATT TCAAGAAATA     240
CATCGGTTTT GACGAGCCTG ACGAAGCGAA GGATGATTCC AGGGTTGGTG CAGATGATGC     300
TGGTTCTTTT GAACATTATG GGACAATGAT TCTGGGCCTT TGTGGGAGA  ATGTTATGAA     360
CGTGATCGTG GTGGCTGCTG AATGTTCTCC ATGGTGCAAA ACAGGTGGTC TTGGAGATGT     420
TGTGGGAGCT TTACCCAAGG CTTTAGCGAG AAGAGGACAT CGTGTTATGG TTGTGGTACC     480
AAGGTATGGG GACTATGTGG AAGCCTTTGA TATGGGAATC CGGAAATACT ACAAAGCTGC     540
AGGACAGGAC CTAGAAGTGA ACTATTTCCA TGCATTTATT GATGGAGTCG ACTTTGTGTT     600
CATTGATGCC TCTTTCCGGC ACCGTCAAGA TGACATATAT GGGGAAGTA  GGCAGGAAAT     660
CATGAAGCGC ATGATTTTGT TTGCAAGGT  TGCTGTTGAG GTTCCTTGGC ACGTTCCATG     720
CGGTGGTGTG TGCTACGGAG ATGGAAATTT GGTGTTCATT GCCATGAATT GGCACACTGC     780
ACTCCTGCCT GTTTATCTGA AGGCATATTA CAGAGACCAT GGGTTAATGC AGTACACTCG     840
CTCCGTCCTC GTCATACATA ACATCGGCCA CCAGGGCCGT GGTCCTGTAC ATGAATTCCC     900
GTACATGGAC TTGCTGAACA CTAACCTTCA ACATTTCGAG CTGTACGATC CGTCGGTGG     960
CGAGCACGCC AACATCTTTG CCGCGTGTGT TCTGAAGATG GCAGACCGGG TGGTGACTGT    1020
CAGCCGCGGC TACCTGTGGG AGCTGAAGAC AGTGGAAGGC GGCTGGGGCC TCCACGACAT    1080
CATCCGTTCT AACGACTGGA AGATCAATGG CATTCGTGAA CGCATCGACC ACCAGGAGTG    1140
GAACCCCAAG GTGGACGTGC ACCTGCGGTC GGACGGCTAC ACCAACTACT CCCTCGAGAC    1200
ACTCGACGCT GGAAAGCGGC AGTGCAAGGC GGCCCTGCAG CGGGACGTGG GCCTGGAAGT    1260
GCGCGACGAC GTGCCGCTGC TCGGCTTCAT CGGGCGTCTG GATGGACAGA AGGGCGTGGA    1320
CATCATCGGG GACGCGATGC CGTGGATCGC GGGGCAGGAC GTGCAGCTGG TGATGCTGGG    1380
CACCGGCCCA CCTGACCTGG AACGAATGCT GCAGCACTTG GAGCGGGAGC ATCCCAACAA    1440
GGTGCGCGGG TGGGTCGGGT TCTCGGTCCT AATGGTGCAT CGCATCACGC CGGGCGCCAG    1500
CGTGCTGGTG ATGCCCTCCC GCTTCGCCGG CGGGCTGAAC CAGCTCTACG CGATGGCATA    1560
CGGCACCGTC CCTGTGGTGC ACGCCGTGGG CGGGCTCAGG GACACCGTGG CGCCGTTCGA    1620
CCCGTTCGGC GACGCCGGGC TCGGGTGGAC TTTTGACCGC GCCGAGGCCA ACAAGCTGAT    1680
CGAGGTGCTC AGCCACTGCC TCGACACGTA CCGAAACTAC GAGGAGAGCT GGAAGAGTCT    1740
CCAGGCGCGC GGCATGTCGC AGAACCTCAG CTGGGACCAC GCGGCTGAGC TCTACGAGGA    1800
CGTCCTTGTC AAGTACCAGT GGTGAACCCT CCGCCCTCCG CATCAATATC TTCGGTTTGA    1860
TCCCATTGTA CATCGCCCTT TGACGGTCTC GGTGAAGAAC TTCATATGCA GTGCCGTGCT    1920
GGGGCGGTAG CAGTACTATG GGATTGCATT GAGCTGTGTC ACTATGTGCT TTCGACAGGA    1980
CAGTAGTGAA GGTTCTATGC AAGTTTATTT TTTTTTTCAT TACTGATATT TGGAATGTCA    2040
ACACAATAAA TAACTACTAT GTGTTTCGTA AGTAAAAAAA AAAAA                    2085
```

( 2 ) INFORMATION FOR SEQ ID NO:3:

( i ) SEQUENCE CHARACTERISTICS:
        ( A ) LENGTH: 2380 base pairs
        ( B ) TYPE: nucleic acid
        ( C ) STRANDEDNESS: both
        ( D ) TOPOLOGY: linear ( i i ) MOLECULE TYPE: cDNA -continued ( x i ) SEQUENCE DESCRIPTION: SEQ ID NO:3:

GCNGCNGCNT GGTRRGCNYT NGTNCARGCN GARGCNGCNG TNGCNTRRGG NATHCCNATG 60

CCNGGNGCNA THWSNWSNWS NWSNWSNGCN TTYYTNYTNC CNGTNGCNWS NWSNWSNCCN 120

MGNMGNMGNM GNGGNWSNGT NGGNGCNGCN YTNMGNWSNT AYGGNTAYWS NGGNGCNGAR 180

YTNMGNYTNC AYTGGGCNMG NMGNGGNCCN CCNCARGAYG GNGCNGCNWS NGTNMGNGCN 240

GCNGCNGCNC CNGCNGGNGG NGARWSNGAR GARGCNGCNA ARWSNWSNWS NWSNWSNCAR 300

GCNGGNGCNG TNCARGGNWS NACNGCNAAR GCNGTNGAYW SNGCNWSNCC NCCNAAYCCN 360

YTNACNWSNG CNCCNAARCA RWSNCARWSN GCNGCNATGC ARAAYGGNAC NWSNGGNGGN 420

WSNWSNGCNW SNACNGCNGC NCCNGTNWSN GGNCCNAARG CNGAYCAYCC NWSNGCNCCN 480

GTNACNAARM GNGARATHGA YGCNWSNGCN GTNAARCCNG ARCCNGCNGG NGAYGAYGCN 540

MGNCCNGTNG ARWSNATHGG NATHGCNGAR CCNGTNGAYG CNAARGCNGA YGCNGCNCCN 600

GCNACNGAYG CNGCNGCNWS NGCNCCNTAY GAYMGNGARG AYAAYGARCC NGGNCCNYTN 660

GCNGGNCCNA AYGTNATGAA YGTNGTNGTN GTNGCNWSNG ARTGYGCNCC NTTYTGYAAR 720

ACNGGNGGNY TNGGNGAYGT NGTNGGNGCN YTNCCNAARG CNYTNGCNMG NMGNGGNCAY 780

MGNGTNATGG TNGTNATHCC NMGNTAYGGN GARTAYGCNG ARGCNMGNGA YYTNGGNGTN 840

MGNMGNMGNT AYAARGTNGC NGGNCARGAY WSNGARGTNA CNTAYTTYCA YWSNTAYATH 900

GAYGGNGTNG AYTTYGTNTT YGTNGARGCN CCNCCNTTYM GNCAYMGNCA YAAYAAYATH 960

TAYGGNGGNG ARMGNYTNGA YATHYTNAAR MGNATGATHY TNTTYTGYAA RGCNGCNGTN 1020

GARGTNCCNT GGTAYGCNCC NTGYGGNGGN ACNGTNTAYG GNGAYGGNAA YYTNGTNTTY 1080

ATHGCNAAYG AYTGGCAYAC NGCNYTNYTN CCNGTNTAYY TNAARGCNTA YTAYMGNGAY 1140

AAYGGNYTNA TGCARTAYGC NMGNWSNGTN YTNGTNATHC AYAAYATHGC NCAYCARGGN 1200

MGNGGNCCNG TNGAYGAYTT YGTNAAYTTY GAYYTNCCNG ARCAYTAYAT HGAYCAYTTY 1260

AARYTNTAYG AYAAYATHGG NGGNGAYCAY WSNAAYGTNT TYGCNGCNGG NYTNAARACN 1320

GCNGAYMGNG TNGTNACNGT NWSNAAYGGN TAYATGTGGG ARYTNAARAC NWSNGARGGN 1380

GGNTGGGGNY TNCAYGAYAT HATHAAYCAR AAYGAYTGGA ARYTNCARGG NATHGTNAAY 1440

GGNATHGAYA TGWSNGARTG GAAYCCNGCN GTNGAYGTNC AYYTNCAYWS NGAYGAYTAY 1500

ACNAAYTAYA CNTTYGARAC NYTNGAYACN GGNAARMGNC ARTGYAARGC NGCNYTNCAR 1560

MGNCARYTNG GNYTNCARGT NMGNGAYGAY GTNCCNYTNA THGGNTTYAT HGGNMGNYTN 1620

GAYCAYCARA ARGGNGTNGA YATHATHGCN GAYGCNATHC AYTGGATHGC NGGNCARGAY 1680

GTNCARYTNG TNATGYTNGG NACNGGNMGN GCNGAYYTNG ARGAYATGYT NMGNMGNTTY 1740

GARWSNGARC AYWSNGAYAA RGTNMGNGCN TGGGTNGGNT TYWSNGTNCC NYTNGCNCAY 1800

MGNATHACNG CNGGNGCNGA YATHYTNYTN ATGCCNWSNM GNTTYGARCC NTGYGGNYTN 1860

AAYCARYTNT AYGCNATGGC NTAYGGNACN GTNCCNGTNG TNCAYGCNGT NGGNGGNYTN 1920

MGNGAYACNG TNGCNCCNTT YGAYCCNTTY AAYGAYACNG GNYTNGGNTG GACNTTYGAY 1980

MGNGCNGARG CNAAYMGNAT GATHGAYGCN YTNWSNCAYT GYYTNACNAC NTAYMGNAAY 2040

TAYAARGARW SNTGGMGNGC NTGYMGNGCN MGNGGNATGG CNGARGAYYT NWSNTGGGAY 2100

CAYGCNGCNG TNYTNTAYGA RGAYGTNYTN GTNAARGCNA ARTAYCARTG GTRRGCNAAY 2160

TRRYTNGCNA CNMGNMGNMG NWSNTGYMGN MGNACNTGGA CNYTNTTYMG NMGNYTNTTY 2220

WSNYTNGCNG CNYTNATGMG NGCNWSNCAY YTNMGNMGNG CNGAYGGNMG NMGNTGGYTN 2280

GCNTAYMGNY TNMGNMGNYT NMGNGCNYTN GGNATHTGGG CNGGNACNAT GATGCCNYTN 2340

GGNACNGGNM GNGGNGTNGT NTRRTAYGAR ACNGAYGGNG 2380

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Lys Asn Tyr Ala Asn Ala Phe Tyr Thr Glu Thr His Ile
1               5                   10

( 2 ) INFORMATION FOR SEQ ID NO:5:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Glu Leu Gly Gly Tyr Ile Tyr Gly Gln Asn Asp Met Phe Val Val Asn
1               5                   10                  15

Asn Asp His Ala Ser Leu Val Pro Val Leu Leu Ala Ala Lys Tyr Ile
            20                  25                  30

Arg ( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Glu Val Thr Thr Ala Glu Gly Gly Ser Gly Leu Asn Glu Leu Leu
1               5                   10                  15

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Gly Lys Ile Asp Asn Thr Val Val Val Ala Ser Glu Gln Asp Ser Tyr
1               5                   10                  15

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Gly Val Asn Asn Gln Phe Glu Ser Gln Tyr Asp Lys Val
1               5                   10

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Asp Ala Glu Ala Xaa Phe Asn Glu Lys
1               5

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Tyr Glu Glu Leu Gln Ile Thr Ala Gly Arg
1               5                   10

( 2 ) INFORMATION FOR SEQ ID NO:11:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Gly Leu Val Val Thr Arg Asp Arg Asp Arg Ile Gln Xaa Val Ala Ser
1               5                   10                  15

Asn Arg ( 2 ) INFORMATION FOR SEQ ID NO:12:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Ala Ala Ala Arg Lys Ala Val Met Val Pro Glu Gly Glu Asn Arg Glu
1               5                   10                  15

Phe Val Lys Tyr Leu Phe
                20

( 2 ) INFORMATION FOR SEQ ID NO:13:

( i ) SEQUENCE CHARACTERISTICS:

(A) LENGTH: 13 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:13:

Val Arg Pro Pro Pro Xaa Asp Gly Asn Gly Ile Phe Ile
1               5                       10

(2) INFORMATION FOR SEQ ID NO:14:

(i) SEQUENCE CHARACTERISTICS:
    (A) LENGTH: 7 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:14:

Gln His Leu Xaa Gln Tyr Tyr
1               5

(2) INFORMATION FOR SEQ ID NO:15:

(i) SEQUENCE CHARACTERISTICS:
    (A) LENGTH: 13 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:15:

Ile Phe Gln Ile Asp Pro Met Leu Ser Thr Tyr Lys Tyr
1               5                       10

(2) INFORMATION FOR SEQ ID NO:16:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:16:

Xaa Xaa Phe Pro Gln Xaa Val Xaa Xaa
1               5

(2) INFORMATION FOR SEQ ID NO:17:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:17:

Ser Xaa Arg Leu Ala Xaa Xaa Met Val Arg
1               5                       10

(2) INFORMATION FOR SEQ ID NO:18:

(i) SEQUENCE CHARACTERISTICS:

(A) LENGTH: 71 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

GGYGGRCTWG GAGATGTTTG TGGWTCACTC CCAATTGCTC TKGCTCTTCG TGGWCATCGT 60

GTKATGGTTG T 71

(2) INFORMATION FOR SEQ ID NO:19:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

Cys Val Ala Glu Leu Ser Arg Glu Gly Pro Ala Pro Arg
1               5                   10

(2) INFORMATION FOR SEQ ID NO:20:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:20:

Cys Val Ala Glu Leu Ser Arg Glu Gly Pro Ala Pro Arg
1               5                   10

(2) INFORMATION FOR SEQ ID NO:21:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:21:

Lys Xaa Tyr Ala Asn Ala Phe Tyr Thr Glu Thr His Ile
1               5                   10

(2) INFORMATION FOR SEQ ID NO:22:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

Lys Asn Tyr Ala Asn Ala Phe Tyr Ser Glu Lys His Ile
1               5                   10

(2) INFORMATION FOR SEQ ID NO:23:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:23:

Glu Val Thr Thr Ala Glu Gly Gly Ser Gly Leu Asn Glu Leu Leu
1               5                   10                  15

( 2 ) INFORMATION FOR SEQ ID NO:24:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:24:

Glu Val Thr Thr Ala Glu Gly Gly Gln Gly Leu Asn Glu Leu Leu
1               5                   10                  15

( 2 ) INFORMATION FOR SEQ ID NO:25:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:25:

Glu Leu Gly Gly Tyr Ile Tyr Gly Ala Asn Xaa Met Phe Val Val Asn
1               5                   10                  15

Xaa Xaa His Ala Ser Leu Val Pro Val Leu Leu Ala Ala Lys Tyr
                20              25                  30

( 2 ) INFORMATION FOR SEQ ID NO:26:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:26:

Glu Leu Gly Gly Tyr Ile Tyr Gly Gln Asn Cys Met Leu Val Val Asn
1               5                   10                  15

Asp Trp His Ala Ser Leu Glu Pro Val Leu Leu Ala Ala Lys Tyr
                20              25                  30

( 2 ) INFORMATION FOR SEQ ID NO:27:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:27:

```
        Gly  Lys  Ile  Asp  Asn  Thr  Val  Val  Val  Ala  Ser  Glu  Gln  Asp  Ser  Tyr
        1                  5                       10                      15
```

(2) INFORMATION FOR SEQ ID NO:28:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
        Gly  Ser  Ile  Asp  Asn  Thr  Val  Val  Val  Ala  Ser  Glu  Gln  Asp  Ser  Glu
        1                  5                       10                      15
```

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
        Gly  Leu  Val  Val  Thr  Arg  Asp  Arg  Asp  Arg  Ile  Gln  Xaa  Val  Ala  Ser
        1                  5                       10                      15

Asn  Arg
```

(2) INFORMATION FOR SEQ ID NO:30:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
        Gly  Ala  Val  Val  Thr  Ala  Asp  Arg  Ile  Val  Thr  Val  Ser  Lys  Gly  Tyr
        1                  5                       10                      15

Ser
```

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

SRCGNYAMNY GTNNNNNNG GRDTV          25

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:32:

Gly Glu Asn Val Met Asn Val Ile Val Val
1               5                   10

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Cys Val Ala Glu Leu Ser Arg Glu Gly Pro
1               5                   10

( 2 ) INFORMATION FOR SEQ ID NO:34:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

Gly Ser Val Gly Ala Ala Leu Arg Ser Tyr
1               5                   10

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

Ala Ser Ala Gly Met Asn Val Val Phe Val
1               5                   10

( 2 ) INFORMATION FOR SEQ ID NO:36:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

Met Ala Ser Ser Met Leu Ser Ser Ala Ala Val Ala Thr Arg Thr Asn
1               5                   10                  15

Pro Ala Gln Ala Ser Met Val Ala Pro Phe Thr Gly Leu Lys Ser Ala
                20                  25                  30

Ala Phe Pro Val Ser Arg Lys Gln Asn Leu Asp Ile Thr Ser Ile Ala
            35                  40                  45

Ser Asn Gly Gly Arg Val Gln Cys
        50                  55

( 2 ) INFORMATION FOR SEQ ID NO:37:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

```
Met Ala Pro Thr Val Met Met Ala Ser Ser Ala Thr Ala Thr Arg Thr
1               5                   10                  15

Asn Pro Ala Gln Ala Ser Ala Val Ala Pro Phe Gln Gly Leu Lys Ser
                20                  25                  30

Thr Ala Ser Leu Pro Val Ala Arg Arg Ser Ser Arg Ser Leu Gly Asn
            35                  40                  45

Val Ala Ser Asn Gly Gly Arg Ile Arg Cys
        50                  55
```

( 2 ) INFORMATION FOR SEQ ID NO:38:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
                20                  25                  30

Arg Gly Ala Arg Ala Ser Ala Ala Ala Asp Thr Leu Ser Met Arg Thr
            35                  40                  45

Ala Ser Ala Arg Ala Ala Pro Arg His Gln Gln Gln Ala Arg Arg Gly
        50                  55                  60

Gly Arg Phe Pro Ser Leu Val Val Cys
65              70
```

( 2 ) INFORMATION FOR SEQ ID NO:39:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Met Ala Gln Ile Leu Ala Pro Ser Thr Gln Trp Gln Met Arg Ile Thr
1               5                   10                  15

Lys Thr Ser Pro Cys Ala Thr Pro Ile Thr Ser Lys Met Trp Ser Ser
                20                  25                  30

Leu Val Met Lys Gln Thr Lys Lys Val Ala His Ser Ala Lys Phe Arg
            35                  40                  45

Val Met Ala Val Asn Ser Glu Asn Gly Thr
        50                  55
```

( 2 ) INFORMATION FOR SEQ ID NO:40:

-continued ( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:40:

Cys Val Ala Glu Leu Ser Arg Glu Gly Pro Ala Pro Arg
1               5                   10

( 2 ) INFORMATION FOR SEQ ID NO:41:

( i ) SEQUENCE CHARACTERISTICS:
  ( A ) LENGTH: 33 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:41:

Arg Ala Ser Pro Pro Ser Glu Ser Arg Ala Pro Leu Arg Ala Pro Gln
1               5                   10                  15

Arg Ser Ala Thr Arg Gln His Gln Ala Arg Gln Gly Pro Arg Arg Met
            20                  25                  30

Cys

MODIFICATION OF STARCH SYNTHESIS IN PLANTS

RELATED U.S. APPLICATION DATA

This application is a continuation-in-part of Ser. No. 08/346,602, filed Nov. 29, 1994, pending, which is a continuation-in-part of Ser. No. 08/263,921, filed Jun. 21, 1994, abandoned.

This invention relates to the alteration of the biosynthetic pathway which leads to production of starch in plants. By the term "alteration" we mean a change from normal of the amount or quality of the starch which the plant produces. More particularly, the invention relates to the isolation, purification and characterization of the DNAs encoding several forms of the enzyme soluble starch synthase and the use of those DNAs through genetic modification of the plant genome to alter the starch production.

The invention also relates to novel plants having an improved ability to produce starch including an improved ability to produce structurally-altered starch.

Our previous studies have led to a new understanding of the metabolic pathway of starch synthesis in developing starch storing tissues (Keeling et al, 1988, Plant Physiology, 87:311–319; Keeling, 1989, ed. C. D. Boyer, J. C. Shannon and R. C. Harrison; pp. 63–78, being a presentation at the 4th Annual Penn State Symposium in Plant Physiology).

Starch is an important end-product of carbon fixation during photosynthesis in leaves and is an important storage product in seeds and fruits. In economic terms, the starch produced by the edible portions of three grain crops, wheat, rice and maize, provide approximately two-thirds of the world's food calculated as calories.

Starch is synthesized in the plastid compartment, the chloroplast, in photosynthetic cells or the amyloplast in non-photosynthetic cells. The biochemical pathway of starch biosynthesis in leaves has been well-characterized (FIG. 1). In contrast, little is known of the pathway of starch biosynthesis in storage organs.

Two principal methods for the control of gene expression are known. These are referred to in the art as "antisense downregulation" and "sense downregulation" or "cosuppression". Both of these methods lead to an inhibition of expression of the target gene. Overexpression is achieved by insertion of one or more than one extra copies of the selected gene. Other lesser used methods involve modification of the genetic control elements, the promoter and control sequences, to achieve greater or lesser expression of an inserted gene.

In antisense downregulation, a DNA which is complementary to all or part of the target gene is inserted into the genome in reverse orientation and without its translation initiation signal. The simplest theory is that such an anti-sense gene, which is transcribable but not translatable, produces mRNA which is complementary in sequence to mRNA product transcribed from the endogenous gene: that antisense mRNA then binds with the naturally produced "sense" mRNA to form a duplex which inhibits translation of the natural mRNA to protein. It is not necessary that the inserted antisense gene be equal in length to the endogenous gene sequence: a fragment is sufficient. The size of the fragment does not appear to be particularly important. Fragments as small as 40 or so nucleotides have been reported to be effective. Generally somewhere in the region of 50 nucleotides is accepted as sufficient to obtain the inhibitory effect. However, it has to be said that fewer nucleotides may very well work: a greater number, up to the equivalent of full length, will certainly work. It is usual simply to use a fragment length for which there is a convenient restriction enzyme cleavage site somewhere downstream of fifty nucleotides. The fact that only a fragment of the gene is required means that not all of the gene need be sequenced. It also means that commonly a cDNA will suffice, obviating the need to isolate the full genomic sequence.

The antisense fragment does not have to be precisely the same as the endogenous complementary strand of the target gene. There simply has to be sufficient sequence similarity to achieve inhibition of the target gene. This is an important feature of antisense technology as it permits the use of a sequence which has been derived from one plant species to be effective in another and obviates the need to construct antisense vectors for each individual species of interest. Although sequences isolated from one species may be effective in another, it is not infrequent to find exceptions where the degree of sequence similarity between one species and the other is insufficient for the effect to be obtained. In such cases, it may be necessary to isolate the species-specific homologue.

Antisense downregulation technology is well-established in the art. It is the subject of several textbooks and many hundreds of journal publications. The principal patent reference is European Patent No. 240,208 in the name of Calgene Inc. There is no reason to doubt the operability of antisense technology. It is well-established, used routinely in laboratories around the world and products in which it has been used are on the market.

Both overexpression and downregulation are achieved by "sense" technology. If a full length copy of the target gene is inserted into the genome then a range of phenotypes is obtained, some overexpressing the target gene, some underexpressing. A population of plants produces by this method may then be screened and individual phenotypes isolated. As with antisense, the inserted sequence is lacking in a translation initiation signal. Another similarity with antisense is that the inserted sequence need not be a full length copy. Indeed, it has been found that the distribution of over- and under-expressing phenotypes is skewed in favor of underexpression and this is advantageous when gene inhibition is the desired effect. For overexpression, it is preferable that the inserted copy gene retain its translation initiation codon. The principal patent reference on cosuppression is European Patent 465,572 in the name of DNA Plant Technology Inc. There is no reason to doubt the operability of this technology. It is well-established, used routinely in laboratories around the world and products in which it has been used are on the market.

Sense and antisense gene regulation is reviewed by Bird and Ray in Biotechnology and Genetic Engineering Reviews 9: 207–227 (1991). The use of these techniques to control selected genes in tomato has been described by Gray et.al., Plant Molecular Biology, 19: 69–87 (1992).

Gene control by any of the methods described requires insertion of the sense or antisense sequence, with appropriate promoters and termination sequences containing polyadenylation signals, into the genome of the target plant species by transformation, followed by regeneration of the transformants into whole plants. It is probably fair to say that transformation methods exist for most plant species or can be obtained by adaptation of available methods.

For dicotyledonous plants the most widely used method is Agrobacterium-mediated transformation. This is the best known, most widely studied and, therefore, best understood of all transformation methods. The rhizobacterium *Agrobacterium tumefaciens*, or the related *Agrobacterium rhizogenes*, contain certain plasmids which, in nature, cause the formation of disease symptoms, crown gall or hairy root tumours, in plants which are infected by the bacterium. Part of the mechanism employed by Agrobacterium in pathogenesis is that a section of plasmid DNA which is bounded by right and left border regions is transferred stably into the genome of the infected plant. Therefore, if foreign DNA is inserted into the so-called "transfer" region (T-region) in substitution for the genes normally present therein, that foreign gene will be transferred into the plant genome. There are many hundreds of references in the journal literature, in textbooks and in patents and the methodology is well-established.

The effectiveness of Agrobacterium is restricted to the host range of the microorganism and is thus restricted more or less to dicotyledonous plant species. In general monocotyledonous species, which include the important cereal crops, are not amenable to transformation by the Agrobacterium method. Various methods for the direct insertion of DNA into the nucleus of monocot cells are known.

In the ballistic method, microparticles of dense material, usually gold or tungsten, are fired at high velocity at the target cells where they penetrate the cells, opening an aperture in the cell wall through which DNA may enter. The DNA may be coated on to the microparticles or may be added to the culture medium.

In microinjection, the DNA is inserted by injection into individual cells via an ultrafine hollow needle.

Another method, applicable to both monocots and dicots, involves creating a suspension of the target cells in a liquid, adding microscopic needle-like material, such as silicon carbide or silicon nitride "whiskers", and agitating so that the cells and whiskers collide and DNA present in the liquid enters the cell.

In summary, then, the requirements for both sense and antisense technology are known and the methods by which the required sequences may be introduced are known. What remains, then is to identify genes whose regulation will be expected to have a desired effect, isolate them or isolate a fragment of sufficiently effective length, construct a chimeric gene in which the effective fragment is inserted between promoter and termination signals, and insert the construct into cells of the target plant species by transformation. Whole plants may then be regenerated from the transformed cells.

An object of the present invention is to provide DNAs encoding soluble starch synthases.

An further object of the invention is to provide novel plants having an increased capacity to produce starch and a capacity to produce starch with an altered fine structure.

According to the present invention there is provided cDNAs having the sequences of the inserts in plasmids pSSS6, pSSS10.1 and pSSS6.31 and sequences having sufficient similarity such that when inserted into the genome of an organism which produces starch, the synthesis of starch is altered.

The plasmid pSSS6 was deposited under the terms of the Budapest Treaty, with the National Collections of Industrial and Marine Bacteria Limited, 23 St Machar Drive, Aberdeen AB1 2RY, on 13th Jun. 1994, under the Accession Number 40651.

The plasmids pSSS6.31 and pSSS10.1 were deposited under the terms of the Budapest Treaty, with the National Collections of Industrial and Marine Bacteria Limited, 23 St Machar Drive, Aberdeen AB1 2RY, on 22nd Aug. 1994, under the Accession Numbers NCIMB 40679 and 40680 respectively.

The invention also provides the cDNAs, encoding soluble starch synthases which have the sequences SEQ-ID-NO-1, SEQ-ID-NO-2 AND SEQ-ID-NO-3.

The invention also provides transformed plants containing one or more copies of one or more of the said cDNAs in sense or antisense orientation.

The description which follows will describe a method for the isolation of the genes encoding soluble starch synthases from maize.

Figure 2:
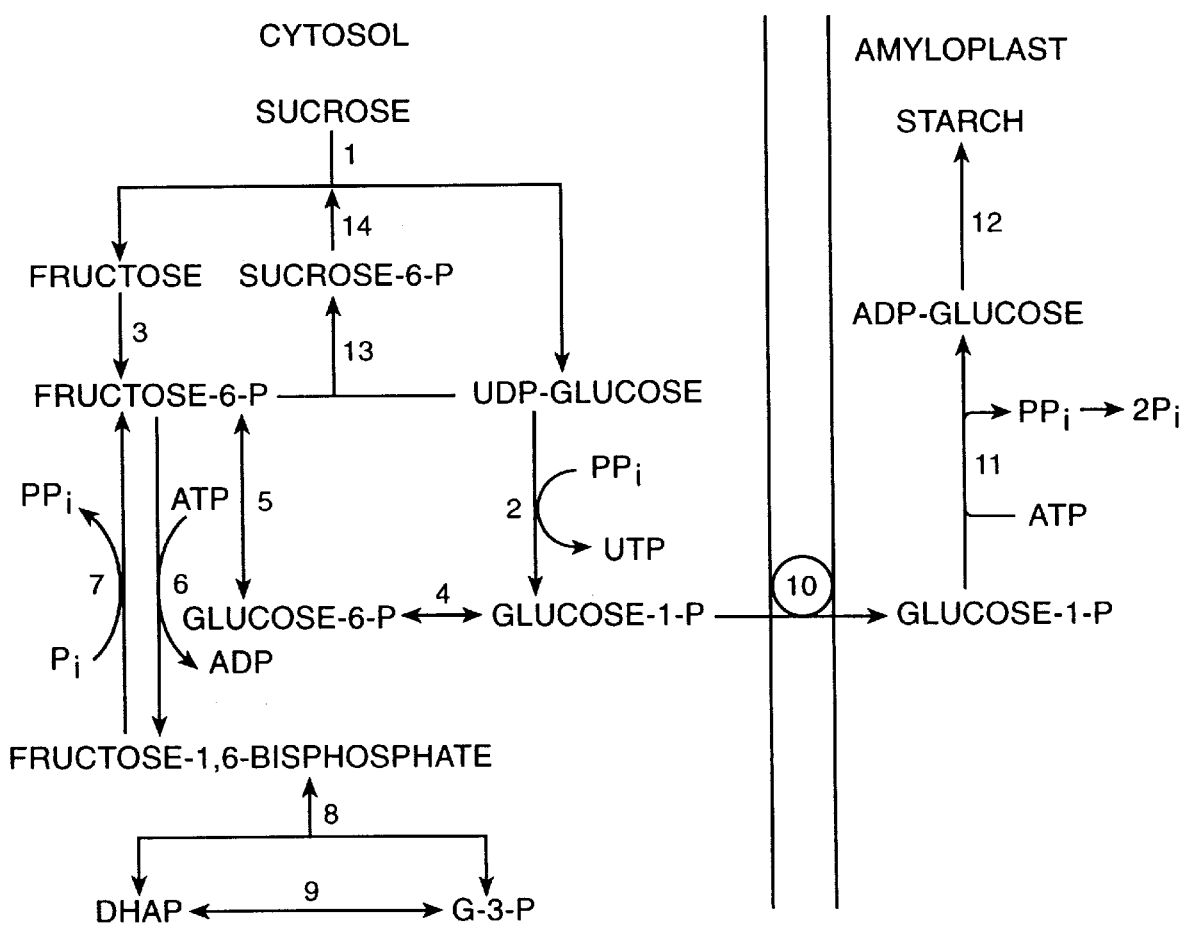

These DNAs can be used for the isolation of the corresponding genomic sequences. Either the cDNAs or the genes can then be used in studies leading to the increase in starch yield. One possible application could be the use of these sequences to increase gene dosage of SSS in transformed crop plants to determine the contribution of SSS to the net regulation of starch biosynthesis, and to modify the levels of starch synthesized by the plant. The introduction of additional copies of SSS genes should produce greater levels of the enzyme in the amyloplasts. Increased gene expression may also be elicited by introducing multiple copies of enhancer sequences into the 5'-untranscribed region of SSS gene. If the enzyme is rate-limiting to starch biosynthesis, then the rate of starch biosynthesis would be expected to increase in the transformed plants. By virtue of this invention it will also be possible to alter the kinetic properties of the endosperm enzyme through protein engineering. Obviously a number of other parameters could also be improved. The present invention will now be described, by way of illustration, by the following Example and with reference to the accompanying drawings of which:

FIG. 1 shows the reactions involved in the biosynthetic pathways of starch and glucose in leaves. The abbreviations used are: G-3-P,glyceraldehyde-3-phosphate; DHAP, dihydroxyacetone phosphate; Pi, orthophosphate; PPi, inorganic pyrophosphate. The reactions are catalyzed by the following enzymes:

1) phosphoglycerate kinase/glyceraldehyde-3-phosphate dehydrogenase
2) triose-phosphate isomerase
3) aldolase
4) fructose-1,6-bisphosphatase
5) hexose phosphate isomerase
6) phosphoglucomutase
7) ADP-glucose pyrophosphorylase
8) starch synthase
9) UDP-glucose pyrophosphorylase
10) sucrose phosphate synthase
11) sucrose phosphatase
12) orthophosphate/triose phosphate translocator
13) inorganic pyrophosphatase FIG. 2 shows the proposed metabolic pathway of starch biosynthesis in wheat endosperm (Keeling et. al. 1988). The abbreviations used are the same as in FIG. 1. The reactions are catalyzed by the following enzymes:

1) sucrose synthase
2) UDP-glucose pyrophosphorylase
3) hexokinase
4) phosphoglucomutase
5) hexose-phosphate isomerase
6) ATP-dependent phosphofructokinase
7) PPi-dependent phosphofructokinase
8) aldolase 9) triose-phosphate isomerase
10) hexose-phosphate translocator (?)
11) ADP-glucose pyrophosphorylase
12) starch synthase
13) sucrose phosphate synthase
14) sucrose phophatase

USE OF SOLUBLE STARCH SYNTHASE OR BRANCHING ENZYME

Using standard cloning techniques, the SSS and BE genes may be isolated. The source of the genes was a US yellow-dent corn line of Zea mays, from which the enzyme protein was purified. Endosperms from the maize line were homogenized in a buffer which maintains the SSS and BE in active form.

Purification of the SSS from maize has been achieved by a combination of ammonium sulphate precipitation, DEAE-cellulose chromatography, gel-filtration, phenyl Superose and FPLC using a Mono-Q column. This results in several hundred-fold purification with yields up to 5%. The SSS polypeptide was a single subunit of molecular weight 76 kDa. Other SSS polypeptides were present in a US dent inbred line at around 60 kDa, 70 kDa and 105 kDa molecular weight.

Ammonium sulphate precipitation of SSS I is best achieved using 10–35% ammonium sulphate which produces a translucent SSS-enriched pellet which is next dialyzed and further fractionated using DEAE-cellulose ion-exchange chromatography (2.5×5 cm column). SSS was eluted with a 150 ml gradient of KCl (0–0.6M) and fractions collected. These steps increase specific activities by up to 12-fold. The DEAE peak fractions were concentrated by precipitation with ammonium sulfate (40%) and the resulting pellet dissolved in buffer and fractionated on a Sephacryl S-200 column (2.5×100 cm) equilibrated with buffer and fractions collected. These steps increase specific activities by up to 8-fold. A Phenyl-Superose column was equilibrated with buffer containing ammonium sulfate. SSSI did not bind and was present in the pass-through fraction. These steps increase specific activities by up to 2-fold. Finally, a Mono-Q column was equilibrated with buffer and charged with the Phenyl-Superose pass-through fraction. The enzymes were eluted from the column using a 12 ml linear gradient of 0–0.5M Kcl and fractions collected. These steps increase specific activities by up to 5-fold.

Purification of the SSS and BE enzymes from the US inbred line B73 identified three SSS and three BE isoforms. FIG. 22 shows the data for SSS; BE behaves similarly. Preliminary investigations have suggested that these isoforms have slightly different temperature optima of activity and also slightly different temperature thresholds for knock-down (Figures).

In the final purification step the SSS or BE preparations were loaded on to SDS PAGE gels. The bands corresponding to the SSS or BE polypeptides were cut out and eluted. The polypeptide was sequenced using standard amino acid sequencing techniques.

In order to produce a pure antigen for antibody production, we decided to use starch granules as our starting-point for isolation of SSS proteins. Kernels were homogenized in buffer by grinding in a Waring blender. The homogenate filtered through miracloth and centrifuged. After discarding the supernatant and the discolored material that overlays the white starch pellet, the pellet was washed twice with buffer and centrifuged. Starch was washed a final time with chilled acetone and following centrifugation, dried under a stream of air before storing at −20 C. Granule protein was extracted by boiling 1.4 g starch for 10 minutes in 50 ml SDS-PAGE sample buffer (2% SDS, 5% 2-mercaptoethanol, 10% glycerol and 62.5 mM Tris/HCl, pH 6.8) which lacked bromophenol blue. After cooling and centrifugation at 25,000 g at 4 C for 15 minutes, the supernatant was mixed with an equal volume of 30% TCA and allowed to stand at 4 C for 1 hour. The solution was centrifuged again and pellet washed twice with 10 ml acetone before resuspension in 1.4 ml SDS-PAGE sample buffer. Following separation of granule-derived proteins by SDS-PAGE, the SSS proteins (eg 60 kDa, 76 kDa etc) bands were electroeluted and used as antigen (three 50 ug doses at 4-week intervals, in New Zealand white rabbits) to generate polyclonal antibodies in a rabbit. The antibodies were then tested for specificity to the SSS or BE polypeptides. Antibodies to the 76 kDa and 86 kDa were monospecific and have enabled a thorough analysis of enzyme activities and expression studies.

N-terminal amino acid sequences were also obtained from the polypeptides. These proteins were shown to be identical with soluble proteins on the basis of (i) N-terminal sequences to the SSSs and BEs purified by conventional means and sequenced were identical to the granule derived proteins, and (ii) protease digests gave peptide maps which were also identical. Full sequencing of the maize polypeptides is continuing.

Amino acid sequencing of the maize BE-86 kDa polypeptide has provisionally yielded the following partial sequence:

For example:

| | | |
|---|---|---|
| SSSI | N-terminal sequence | CVAELSREGPAPR (SEQ ID NO: 40) |
| Internal sequences | | |

1 (SEQ ID NO: 4) K N Y A N A F Y T E T H I
2 (SEQ ID NO: 5) E L G G Y I Y G Q N D M F V V N N D H A S L V P V L L A A K Y I R
3 (SEQ ID NO: 6) E V T T A E G G S G L N E L L
4 (SEQ ID NO: 7) G K I D N T V V V A S E Q D S Y
5 (SEQ ID NO: 8) G V N N Q F E S Q Y D K V
6 (SEQ ID NO: 9) D A E A X F N E K
7 (SEQ ID NO: 10) Y E E L Q I T A G R
8 (SEQ ID NO: 11) G L V V T R D R D R I Q - V A S N R [from SSSI purification]

| | | |
|---|---|---|
| BEII | N-terminal | AAARKAVMVPEGENREFVKYLF |
| Internal sequences | | |

1   V R P P P X D G N G I F I
2   Q H L X Q Y Y
3   I F Q I D P M L S T Y K Y

-continued

New N-terminal sequences to starch granule proteins (as yet not identified)

| | |
|---|---|
| 83kDa N-terminal | E/A?FPQN/AVA/QP/L |
| 91kDa N-terminal | S?RLAV/AV/MMVR |

The antibodies may be used to screen a maize endosperm cDNA library for clones derived from the mRNAs for SSS or BE in an in vitro transcription/translation system. Synthetic oligos may be constructed and used to screen maize endosperm cDNA library. The BE sequence may be compared to the amino acid sequence of maize BEI and BEII published by Baba et al (1991, Biochem Biophys Res Com 181:87–94) and Fisher et al (1993, Plant Physiology 102:1045–1046). The SSS sequence may be compared to the amino acid sequence of pea SSS I and SSS II published by Dry et al (1991, Plant Journal 2:193–202) or rice SSS published by Baba et al (1993, Plant Physiology 103, 565–573). Interestingly, the clone obtained from rice SSS is not correctly identified. The N-terminal sequence AELSREG is stated to be part of the transit peptide sequence of the rice clone. This error must have occurred because of protein isolation problems from rice kernels: presumably a portion of the protein was cleaved prior to isolation. Using our N-terminal sequence, the corrected molecular weight of the rice clone is around 69 kDa and not 55 or 57 kDa as suggested by Baba et al.

cDNA LIBRARY SCREENING AND ISOLATION OF SSS cDNA CLONES

RNA was extracted from 21 DAP endosperm (obtained from the inbred line B73) after removal of pericarp and embryo. The library consisted of ~900,000 recombinant clones. A probe for granule bound starch synthase was generated using PCR and used to screen an aliquot of the library, ~500,000 recombinants. This screening yielded approximately 200 positive signals. Isolation and sequencing of a number showed them to be full length GBSS cDNA clones.

An oligonucleotide was synthesized to N-terminal sequence obtained from the purified SSS protein and used to screen the same aliquot of library as that used for the GBSS screening. No positive signals were obtained. A long oligonucleotide probe was then synthesized to the ADP-ADPG binding region and following sequence, based on a comparison of the sequences published for pea SSS, rice SSS and maize GBSS.

The sequence of the oligonucleotide was GGT/C GGA/G CTA/T GGAGATGTTTGTGGA/T TCACTCCCAATTGCTCTT/G GCTCTTCGTGGA/T CATCGTGTG/T ATGGTTGT. Fifteen strong signals were obtained, all were picked, of these ten plaque purified after two rounds of purification. Restriction analysis of all ten showed them to fall into two classes. Sequence analysis showed both classes to be starch synthases.

Screening of a maize seedling library (Clontech) gave positive signals using 5' probes from one class of clones only.

A cDNA library from the inbred line W64A was screened and full length clones were isolated as judged by comparison with N-terminal sequence.

CHARACTERIZATION OF cDNA CLONES

The isolated cDNAs were sequenced and are given herewith as SEQ-ID-NO-1, NO-2 and NO-3.

For comparison, the deduced amino acid sequences are shown here with the sequences obtained directly from the protein:—

| | |
|---|---|
| CVAELSREGPAPR | peptide derived |
| CVAELSREGPAPR | deduced cDNA 6.4 |
| KXYANAFYTETHI | peptide derived |
| KNYANAFYSEKHI | deduced cDNA 10.52 |
| EVTTAEGGSGLNELL | peptide derived |
| EVTTAEGGQGLNELL | deduced cDNA 10.52 |
| ELGGYIYGANXMFVVNXXHASLVPVLLAAKY | peptide derived |
| ELGGYIYGQNCMLVVNDWHASLEPVLLAAKY | deduced cDNA 10.52 |
| GKIDNTVVVASEQDSY | peptide derived |
| GSIDNTVVVASEQDSE | deduced cDNA10.52 |
| Isolated from soluble 76kDa protein . . . | |
| GLVVTRDRDRIQ-VASNR | peptide derived |
| GAVVTADRIVTVSKGYS | deduced cDNA 10.52 |

Clone SSS6.31 contained none of these internal sequences. The motif for the binding-site of ADPG and ADP, thought to be part of the active site of starch synthases is found in all clones near to the 5' end and is followed by the highly conserved sequence on which the oligonucleotide probe was based. The highly conserved domain SRFEPCGLNQLYAMXYGTXXXXXXXGGLRDTV is present in SSS10.52 but is slightly modified in SSS6.31 in that the EPC motif is replaced with an AG motif.

Expression of maize starch synthases in Escherichia coli BL21(DE3).

These SSS clones have been transfected into E. coli. The SSS activity was measured and are reported in the Table below.

| Plasmids | Maize starch syntase genes | N-terminus | Protein (mg/mL) | Specific Activities* (units/mg Protein) |
|---|---|---|---|---|
| pET21a | Native plasmid | <no insert> | 1.8 | .009 |
| pEXS-3a | MSSSII (MSSS631) | GENVMNVIVV | 2.8 | 0.069 |
| pEXS-8 | MSSSI (MSSS6-4) | CVAELSREGP | 1.9 | 0.097 |
| pEXS-9 | MSSSIII (MSSS5.6) | GSVGAALRSY | 1.8 | 0.515 |
| pEXS-wx | MGBSS (waxy) | ASAGMNVVFV | 2.0 | 0.033 |

*One unit activity is defined as one μmol glucose incorporated into α-1,4 glucan per minute at 25° C. using 5 mg/mL glycogen as primer.

GENE CONSTRUCTS FOR TRANSFORMATION

The gene constructs require the presence of an amyloplast transit peptide to ensure its correct localization in the amyloplast. It is believed that chloroplast transit peptides have similar sequences but other potential sources are available such as that attached to ADPG pyrophosphorylase (Plant Mol. Biol. Reporter (1991) 9, 104–126). Other potential transit peptides are those of small subunit RUBISCO, acetolactate synthase, glyceraldehyde-3P-dehydrogenase and nitrite reductase. For example, Consensus sequence of the transit peptide of small subunit RUBISCO from many genotypes has the sequence:

MASSMLSSAAV-ATRTNPAQAS    MVAPFTGLKSAAFPVSRK    QNLDITSIA SNGGRVQC and the corn small subunit RUBISCO has the sequence:

MAPTVMMASSAT-ATRTNPAQAS    AVAPFQGLKSTASLPVARR    SSRSLGNVA SNGGRIRC

The transit peptide of leaf starch synthase from corn has the sequence:

MA ALATSQLVAT RAGLGVPDAS TFRRGAAQGL RGARASAAAD TLSMRTASARA APRHQQQARR GGRFPSLVVC

The transit peptide of leaf glyceraldehyde-3P-dehydrogenase from corn has the sequence:

MAQILAPS    TQWQMRITKT    SPCATPITSK    MWSSLVMKQT    KKVAHSAKFR VMAVNSENGT

The putative transit peptide from ADPG pyrophosphorylase from wheat has the sequence:

RASPPSESRA PLRAPQRSAT RQHQARQGPR RMC

It is possible however to express the genes constitutively using one of the well-known constitutive promoters such as CaMV35S but there may be biochemical penalties in the plant resulting from increased starch deposition throughout the entire plant. Deposition in the endosperm is much preferred.

Possible promoters for use in the invention include the promoters of the starch synthase gene, bound starch synthase gene, endosperm hsp70 gene, ADPG pyrophosphorylase gene, and the sucrose synthase gene.

| Plasmid name | Promoter | Intron | Targeting | Gene |
|---|---|---|---|---|
| FOR TESTING GENE EXPRESSION IN ENDOSPERM TISSUE: | | | | |
| pHKH1 | CaMV35S | adh1 | WxTrPep | GUS |
| pSh1PIGN | CaMV35S | adh1 | WxTrPep | GUS |
| pSh2PIGN | CaMV35S | adh1 | WxTrPep | GUS |
| FOR TESTING IN SUSPENSION CELL CULTURES: | | | | |
| p***1 | CaMV35S | Sh1 | WxTrPep | GUS |
| p***2 | CaMV35S | adh1 | WxTrPep | GUS |
| FULL VECTORS FOR PLANT TRANSFORMATION | | | | |
| p***21 | Waxy | Sh1 | WxTrPep | SSS and/or BE |
| p***22 | Waxy | Adh1 | WxTrPep | SSS and/or BE |
| p***23 | Sh1 | Sh1 | WxTrPep | SSS and/or BE |
| p***24 | Sh1 | Adh1 | WxTrPep | SSS and/or BE |
| p***25 | Sh2 | Sh1 | WxTrPep | SSS and/or BE |
| p***26 | Sh2 | Adh1 | WxTrPep | SSS and/or BE |
| p***27 | hsp70 | Sh1 | WxTrPep | SSS and/or BE |
| p***28 | hsp70 | Adh1 | WxTrPep | SSS and/or BE |

TRANSFORMATION (i) Insertion of extra copies of the gene

Maize genomic DNAs isolated as above may subsequently be transformed into either protoplasts or other tissues of a maize inbred line or population. The existing gene promoters ensure that the extra genes are expressed only in the developing endosperm at the correct developmental time. The protein sequences likewise ensure that the enzymes are inserted into the amyloplast.

Transgenic maize plants are regenerated and the endosperms of these plants are tested for increased SSS and BE enzyme activity. The kernels are also tested for enhanced rate of starch synthesis at different temperatures. The plants are then included in a breeding program to produce new maize hybrids with higher rates of starch synthesis at temperatures above the normal optimum.

(ii) Insertion of genes specifying SSS and/or BE with higher temperature optima for activity.

This is also achieved by standard cloning techniques. The source of the temperature-stable forms of the SSS or BE or GS genes is any organism that can make starch or glycogen. Potential donor organisms are screened and identified as described above. Thereafter there are two approaches:

(a) via enzyme purification and antibody/sequence generation using the protocol described above.

(b) using SSS and BE and GS cDNAs as heterologous probes to identify the genomic DNAs for SSS and BE and GS in libraries from the organism concerned. The gene transformation, plant regeneration and testing protocols are as described above. In this instance it is necessary to make gene constructs for transformation which contain the regulatory sequences from maize endosperm SSS or BE or another maize endosperm starch synthesis pathway enzyme to ensure expression in endosperm at the correct developmental time (eg, ADPG pyrophosphorylase).

One specific example of this is with the bacterial glycogen synthase enzyme which we have found to be essentially tolerant of temperatures up to 40 C. The nucleotide and amino-acid sequences of glycogen synthase are known (i) from *E. Coli* GenBank/EMBL #JO2616 (Kumar et al, J Biol Chem 34 16256–16259 (1986)). (ii) from rabbit skeletal muscle (Zhang et al, FASEB J 3 2532–2536 1989)), and (iii) from human muscle (Browner et al, Proc Nat Acad 5 cl 86 1443–1447 (1989)). Gene constructs used to transform plants requires the regulatory sequences from maize endosperm SSS or BE or another maize endosperm starch synthesis pathway enzyme to ensure expression in endosperm at the correct development time (eg, ADPG pyrophosphorylase). Furthermore the gene constructs also requires a suitable amyloplast transit-peptide sequence such as from maize endosperm SSS or BE or another maize endosperm starch synthesis pathway enzyme to censure expression of the amyloplast at the correct developmental time (eg, ADPG pyrophosphorylase).

Genetic protein engineering techniques may also be used to alter the amino acid sequence of the SSS or BE or GS enzymes to impart higher temperature optima for activity. The genes for SSS and/or BE and/or GS may be cloned into a bacteria which relies on these enzymes for survival. Selection for bacteria surviving at evaluated temperatures enables the isolation of mutated thermostable enzyme forms. Transformation of maize with the altered genes is carried out as described above.

Genetic protein engineering techniques may also be used to alter the amino acid sequence of the maize SSS or BE enzymes to impart higher temperature optima for activity. The genes for SSS and/or BE may be cloned into bacteria relies on the these enzymes for survival. Selection for bacteria surviving at elevated temperatures enables the isolation of mutated thermostable enzymes forms. Transformation of maize with the altered genes is carried out as described above.

(iii) Changing the ratios of activities of the isoforms of enzymes SSS or BE.

This is also achieved by standard cloning techniques. The source of the SSS or BE genes is maize using the protocol described above. Plants are then transformed by insertion of extra gene copies of the isoforms of SSS, BE enzymes and/or by insertion of anti-sense gene constructs. The gene promoters and other regulatory sequences may also be altered to achieve increased amounts of the enzyme in the recipient plant.

(iv) Insertion of a gene or genes specifying SSS andlor BE and/or GS enzymes with activities which effect a change in the fine structure of the starch.

This is also achieved by standard cloning techniques. The source of the special forms of the SSS or BE or GS genes is any organism that can make starch or glycogen. Potential donor organisms are screened and identified as described above. Thereafter there are two approaches:

(a) via enzyme purification and antibody/sequence generation using the protocol described above. (b) using SSS and BE and GS cDNAs as heterologous probes to identify the genomic DNAs for SSS and BE and GS in libraries from the organism concerned. The gene transformation, plant regeneration and testing protocols are as described above. In this instance it is necessary to make gene constructs for transformation which contain the regulatory sequences from maize endosperm SSS or BE or another maize endosperm starch synthesis pathway enzyme to ensure expression in endosperm at the correct developmental time (eg, ADPG pyrophosphorylase).

Full length clone sequences

SEQ-ID-NO1; DNA; 2992 BP.
CC NOTE: ORIGINAL SEQUENCE NAME WAS SSS1052 and SSS64
SQ SEQUENCE 2992 BP; 758 A; 655 C; 801 G; 776 T; 2 OTHER;

```
     GAATTCGCGG  CCGCCTTATT  TCTGGTTGGC  CACATACATC  ATCCAAAAAA
CTTTATTATT

GAATTACAAC  TAATAAGCAA  TCTAAAAGAG  GGCACCACCA  ATGATGTGTT
GTTGGTAGGA

GGCCGCTGGG  TCTGTCAAAG  CAAGTTGGAC  AAAGGGCAAC  AATTGTTGTA
GTTGTAAGAG

GGTTGCGGGG  TTAGCCGCAA  ACTGCTGGTA  GAAAGGCAGC  AACTGTTGCT
GTGTCAAGAA

GGAAGCACGG  TTTGCTGCAG  CTGTTGTGCC  CTGATGGTTT  GTACCAATGA
CTGCACCAAA

GATAGGGCTG  GCGATTGTTG  AAACAACAAG  GGCGATAAAG  GTATGTTGCT
TGCTGCGATT
```

-continued
Full length clone sequences

```
    GCTTGTTGAA  GCCTATATGG  TTGAAGAGCT  GGGTTTTCAC  ATATTGAAGC
TATAATTGAT
    GGAAGGTATG  GGGGAAGAAG  GGAAGCTATA  GGAGCTTGTG  AGCATTGAGG
GAAAATTGTC
    GCGTTAGCAA  CACATGTAGA  AAGAGCAAGG  AGCATAAGGA  GGGAAAATAT
CTTGGTCGCC
    ATTGTTGCGC  GCGATCCACG  GCCCCCCCCC  CCCGCGCTCC  TGTCTGCTCT
CCCTCTCCGC
    AATGGCGACG  CCCTCGGCCG  TGGGCGCCGC  GTGCCTCCTC  CTCGCGCGGG
NCG CCTGGCC
    GGCCGCCGTC  GGCGACCGGG  CGCGCCCGCG  GAGGCTCCAG  CGCGTGCTGC
GCCGCCGGTG
    CGTCGCGGAG  CTGAGCAGGG  AGGGGCCCGC  GCCGCGCCCG  CTGCCACCCG
CGCTGCTGGC
    GCCCCCGCTC  GTGCCCGGCT  TCCTCGCGCC  GCCGGCCGAG  CCCACGGGTG
AGCCGGCATC
    GACGCCGCCG  CCCGTGCCCG  ACGCCGGCCT  GGGGGACCTC  GGTCTCGAAC
CTGAAGGGAT
    TGCTGAAGGT  TCCATCGATA  ACACAGTAGT  TGTGGCAAGT  GAGCAAGATT
CTGAGATTGT
    GGTTGGAAAG  GAGCAAGCTC  GAGCTAAAGT  AACACAAAGC  ATTGTCTTTG
TAACCGGCGA
    AGCTTCTCCT  TAATCGAAAG  TCTGGGGGTC  TAGGAGATGT  TTGTGGTTCA
TTGCCAGTTG
    CTCTTGCTGC  TCGCGGTCAC  CGTGTGATGG  TTGTAATGCC  CAGACATTTA
AATGGTACCT
    CCGATAAGAA  TTATGCAAAT  GCATTTTACT  CAGAAAAACA  CATTCGGATT
CCATTCTTTG
    GCGGTGAACA  TGAAGTTACC  TTCTTCCATG  AGTATAGAGA  TTCAGTTGAC
TGGGTGTTTG
    TTGATCATCC  CTCATATCAC  AGACCTGGAA  ATTTATATGG  AGATAAGTTT
GGTGCTTTTG
    GTGATAATCA  GTTCAGATAC  ACACTCCTTT  GCTATGCTGC  ATGTGAGGCT
CCTTTGGTCC
    TTGAATTGGG  AGGATATATT  TATGGACAGA  ATTGCATGTT  GGTTGTCAAT
GATTGGCATG
    CCAGTCTAGA  GCCAGTCCTT  CTTGCTGCAA  AATATAGACC  ATATGGTGTT
TATAAAGACT
    CCCGCAGCAT  TCTTGTAATA  CATAATTTAG  CACATCAGGG  TGTAGAGCCT
GCAAGCACAT
    ATCCTGACCT  TGGGTTGCCA  CCTGAATGGT  ATGGAGCTCT  GGAGTGGGTA
```

-continued
Full length clone sequences

TTCCCTGAAT

GGGCGAGGAG GCATGCCCTT GACAAGGGTG AGGCAGTTAA TTTTTTGAAA GGTGCAGTTG

TGACAGCAGA TCGAATCGTG ACTGTCAGTA AGGGTTATTC ATGGGAGGTC ACAACTGCTG

AAGGTGGACA GGGCCTCAAT GAGCTCTTAA GCTCCAGAAA GAGTGTATTA AACGGAATTG

TAAATGGAAT TGACATTAAT GATTGGAACC CTGCCACAGA CAAATGTATC CCCTGTCATT

ATTCTGTTGA TGACCTCTCT TGAAAGGCTA AATGTAAAGG TGCATTGCAG AAGGAGCTGG

GTTTACCTAT AAGGCCTGAT GTTCCTCTGA TTGGCTTTAT TGGAAGATTG GATTATCAGA

AAGGCATTGA TCTCATTCAA CTTATCATAC CAGATCTCAT GCGGAAGAAT GTTCAA TTTG

TCATGCTTGG ATCTGGTGAC CCAGAGCTTG AAGATTGGAT GAGATCTACA GAGTCGATCT

TCAAGGATAA ATTTCGTGGA TGGGTTGGAT TTAGTGTTCC AGTTTCCCAC CGAATAACTG

CGGCTGGCGA TATATTGTTA ATGCCATCCA GATTCGAACC TTGTGGTCTC AATCAGCTAT

ATGCTATGCA GTATGGCACA GTTCCTGTTG TCCATGCAAC TGGGGGCCTT AGAGATACCG

TGGAGAACTT CAACCCTTTC GGTGAGAATG GAGAGCAGGG TACAGGGTGG GCATTCGCAC

CCCTAACCAC AGAAAACATG TTTGTGGACA TTGCGAACTG CAATATCTAC ATACAGGGAA

CACAAGTAAT AATGGGAAGG GCTAATGAAG CCAGGCATGT CAAAAGAGTT CACGTGGGAC

CATGCCGCTG AACAATACGA ACAAATCTTC CAGTGGGCCT TCATCGGATC GACCCGATGT

TCAATGGAAA AAAGGGACCA AAGTTGGTTG GTTCCTTGAA GATTATCAGT TCATCATCCT

ATAGTAAGCT GAATGATGAA AGAAAACCCC TGTACATTAC ATGGAAGGCA GACCGGCTAT

TGGCTCCATT GCTCCAATGT CTGCTTTGGC TGCCTTGCCT CGATGGACCG GATGCAGTGA

GGAATCCAGN CGAACGACAG TTTTGAAGGA TAGGAAGGGG AGCTGGAAGC AGTCACGCAG

GCAGGCAAGC CTTCGCCGTT AATTCATATG GAACAAGCTG GAGTCAGTTT CTGCTGTGCC

-continued
Full length clone sequences

```
     ACTCACTGTT  TACCTTAAGA  TTATTACCTG  TGTTGTTCTC  CTTTGCTCGT
TAGGGCTGAT

AACATAATGA  CTCATTAAGA  ATATAATTCA  CTCTGCCTCG  TTTTTAATCT
TAAGTGAAGT

CGAGATCTAC  TTCGTCATTC  CTTCCCCGTT  TAAAAAAAAA  AAAAAAAAAA
AA
```

SEQ-ID-NO2; DNA; 2085 BP.
CC NOTE: ORIGINAL SEQUENCE NAME WAS SSS CLONE 6.31
SQ SEQUENCE 2085 BP; 456 A; 521 C; 629 G; 479 T; 0 OTHER;

```
     AACGCCGCAT  TGGCACGTTG  AGATCAAGTC  CATCGTCGCC  GCGCCGCCGA
CGAGCATAGT

GAAGTTCCCA  GGGCGCGGGC  TACAGGATGA  TCCTTCCCTC  TGGGACATAG
CGCCGGAGAC

TGTCCTCCCA  GCCCCGAAGC  CACTGCATGA  ATCGCCTGCG  GTTGACGGAG
ATTCAAATGG

AATTGCACCT  CCTACAGTTG  AGCCATTAGT  ACAGGAGGCC  ACTTGGGATT
TCAAGAAATA

CATCGGTTTT  GACGAGCCTG  ACGAAGCGAA  GGATGATTCC  AGGGTTGGTG
CAGATGATGC

TGGTTCTTTT  GAACATTATG  GGACAATGAT  TCTGGGCCTT  TGTGGGGAGA
ATGTTATGAA

CGTGATCGTG  GTGGCTGCTG  AATGTTCTCC  ATGGTGCAAA  ACAGGTGGTC
TTGGAGATGT

TGTGGGAGCT  TTACCCAAGG  CTTTAGCGAG  AAGAGGACAT  CGTGTTATGG
TTGTGGTACC

AAGGTATGGG  GACTATGTGG  AAGCCTTTGA  TATGGGAATC  CGGAAATACT
ACAAAGCTGC

AGGACAGGAC  CTAGAAGTGA  ACTATTTCCA  TGCATTTATT  GATGGAGTCG
ACTTTGTGTT

CATTGATGCC  TCTTTCCGGC  ACCGTCAAGA  TGACATATAT  GGGGGAAGTA
GGCAGGAAAT

CATGAAGCGC  ATGATTTTGT  TTTGCAAGGT  TGCTGTTGAG  GTTCCTTGGC
ACGTTCCATG

CGGTGGTGTG  TGCTACGGAG  ATGGAAATTT  GGTGTTCATT  GCCATGAATT
GGCACACTGC

ACTCCTGCCT  GTTTATCTGA  AGGCATATTA  CAGAGACCAT  GGGTTAATGC
AGTACACTCG

CTCCGTCCTC  GTCATACATA  ACATCGGCCA  CCAGGGCCGT  GGTCCTGTAC
ATGAATTCCC

GTACATGGAC  TTGCTGAACA  CTAACCTTCA  ACATTTCGAG  CTGTACGATC
CCGTCGGTGG

CGAGCACGCC  AACATCTTTG  CCGCGTGTGT  TCTGAAGATG  GCAGACCGGG
```

-continued
Full length clone sequences

TGGTGACTGT

CAGCCGCGGC TACCTGTGGG AGCTGAAGAC AGTGGAAGGC GGCTGGGGCC
TCCACGACAT

CATCCGTTCT AACGACTGGA AGATCAATGG CATTCGTGAA CGCATCGACC
ACCAGGAGTG

GAACCCCAAG GTGGACGTGC ACCTGCGGTC GGACGGCTAC ACCAACTACT
CCCTCGAGAC

ACTCGACGCT GGAAAGCGGC AGTGCAAGGC GGCCCTGCAG CGGGACGTGG
GCCTGGAAGT

GCGCGACGAC GTGCCGCTGC TCGGCTTCAT CGGGCGTCTG GATGGACAGA
AGGGCGTGGA

CATCATCGGG GACGCGATGC CGTGGATCGC GGGGCAGGAC GTGCAGCTGG
TGATGCTGGG

CACCGGCCCA CCTGACCTGG AACGAATGCT GCAGCACTTG GAGCGGGAGC
ATCCCAACAA

GGTGCGCGGG TGGGTCGGGT TCTCGGTCCT AATGGTGCAT CGCATCACGC
CGGGCGCCAG

CGTGCTGGTG ATGCCCTCCC GCTTCGCCGG CGGGCTGAAC CAGCTCTACG
CGATGGCATA

CGGCACCGTC CCTGTGGTGC ACGCCGTGGG CGGGCTCAGG GACACCGTGG
CGCCGTTCGA

CCCGTTCGGC GACGCCGGGC TCGGGTGGAC TTTTGACCGC GCCGAGGCCA
ACAAGCTGAT

CGAGGTGCTC AGCCACTGCC TCGACACGTA CCGAAACTAC GAGGAGAGCT
GGAAGAGTCT

CCAGGCGCGC GGCATGTCGC AGAACCTCAG CTGGGACCAC GCGGCTGAGC
TCTACGAGGA

CGTCCTTGTC AAGTACCAGT GGTGAACCCT CCGCCCTCCG CATCAATATG
TTCGGTTTGA

TCCCATTGTA CATCGCCCTT TGACGGTCTC GGTGAAGAAC TTCATATGCA
GTGCCGTGCT

GGGGCGGTAG CAGTACTATG GGATTGCATT GAGCTGTGTC ACTATGTGCT
TTCGACAGGA

CAGTAGTGAA GGTTCTATGC AAGTTTATTT TTTTTTTCAT TACTGATATT
TGGAATGTCA

ACACAATAAA TAACTACTAT GTGTTTCGTA AGTAAAAAAA AAAAA

SEQ-ID-NO3: 2478 bp DNA 04-DEC-1995
CC NOTE: ORIGINAL SEQUENCE NAME WAS SSS56
SUMMARY #Molecular-weight 89141 #Length 826 #Checksum 2983
BASE COUNT 347 A 276 C 533 G 290 T
ORIGIN

1 GCNGCNGCNT GGTRRGCNYT NGTNCARGCN GARGCNGCNG TNGCNTRRGG
NATHCCNATG

-continued
Full length clone sequences

```
 61 CCNGGNGCNA  THWSNWSNWS  NWSNWSNGCN  TTYYTNYTNC  CNGTNGCNWS
NWSNWSNCCN

121    MGNMGNMGNM  GNGGNWSNGT  NGGNGCNGCN  YTNMGNWSNT
AYGGNTAYWS    NGGNGCNGAR

181    YTNMGNYTNC  AYTGGGCNMG  NMGNGGNCCN  CCNCARGAYG
GNGCNGCNWS    NGTNMGNGCN

241    GCNGCNGCNC  CNGCNGGNGG  NGARWSNGAR  GARGCNGCNA
ARWSNWSNWS    NWSNWSNCAR

301    GCNGGNGCNG  TNCARGGNWS  NACNGCNAAR  GCNGTNGAYW
SNGCNWSNCC    NCCNAAYCCN

361    YTNACNWSNG  CNCCNAARCA  RWSNCARWSN  GCNGCNATGC
ARAAYGGNAC    NWSNGGNGGN

421    WSNWSNGCNW  SNACNGCNGC  NCCNGTNWSN  GGNCCNAARG
CNGAYCAYCC    NWSNGCNCCN

481    GTNACNAARM  GNGARATHGA  YGCNWSNGCN  GTNAARCCNG
ARCCNGCNGG    NGAYGAYGCN

541    MGNCCNGTNG  ARWSNATHGG  NATHGCNGAR  CCNGTNGAYG
CNAARGCNGA    YGCNGCNCCN

601    GCNACNGAYG  CNGCNGCNWS  NGCNCCNTAY  GAYMGNGARG
AYAAYGARCC    NGGNCCNYTN

661    GCNGGNCCNA  AYGTNATGAA  YGTNGTNGTN  GTNGCNWSNG
ARTGYGCNCC    NTTYTGYAAR

721    ACNGGNGGNY  TNGGNGAYGT  NGTNGGNGCN  YTNCCNAARG
CNYTNGCNMG    NMGNGGNCAY

781    MGNGTNATGG  TNGTNATHCC  NMGNTAYGGN  GARTAYGCNG
ARGCNMGNGA    YYTNGGNGTN

841    MGNMGNMGNT  AYAARGTNGC  NGGNCARGAY  WSNGARGTNA
CTNAYTTYCA    YWSNTAYATH

901    GAYGGNGTNG  AYTTYGTNTT  YGTNGARGCN  CCNCCNTTYM
GNCAYMGNCA    YAAYAAYATH

961    TAYGGNGGNG  ARMGNYTNGA  YATHYTNAAR  MGNATGATHY
TNTTYTGYAA    RGCNGCNGTN

1021 GARGTNCCNT  GGTAYGCNCC  NTGYGGNGGN  ACNGTNTAYG
GNGAYGGNAA    YYTNGTNTTY
```

-continued
Full length clone sequences

```
1081   ATHGCNAAYG   AYTGGCAYAC   NGCNYTNYTN   CCNGTNTAYY
TNAARGCNTA   YTAYMGNGAY

1141   AAYGGNYTNA   TGCARTAYGC   NMGNWSNGTN   YTNGTNATHC
AYAAYATHGC   NCAYCARGGN

1201   MGNGGNCCNG   TNGAYGAYTT   YGTNAAYTTY   GAYYTNCCNG
ARCAYTAYAT   HGAYCAYTTY

1261   AARYTNTAYG   AYAAYATHGG   NGGNGAYCAY   WSNAAYGTNT
TYGCNGCNGG   NYTNAARACN

1321   GCNGAYMGNG   TNGTNACNGT   NWSNAAYGGN   TAYATGTGGG
ARYTNAARAC   NWSNGARGGN

1381   GGNTGGGGNY   TNCAYGAYAT   HATHAAYCAR   AAYGAYTGGA
ARYTNCARGG   NATHGTNAAY

1441   GGNATHGAYA • TGWSNGARTG   GAAYCCNGCN   GTNGAYGTNC
AYYTNCAYWS   NGAYGAYTAY

1501   ACNAAYTAYA   CNTTYGARAC   NYTNGAYACN   GGNAARMGNC
ARTGYAARGC   NGCNYTNCAR

1561   MGNCARYTNG   GNYTNCARGT   NMGNGAYGAY   GTNCCNYTNA
THGGNTTYAT   HGGNMGNYTN

1621   GAYCAYCARA   ARGGNGTNGA   YATHATHGCN   GAYGCNATHC
AYTGGATHGC   NGGNCARGAY

1681   GTNCARYTNG   TNATGYTNGG   NACNGGNMGN   GCNGAYYTNG
ARGAYATGYT   NMGNMGNTTY

1741   GARWSNGARC   AYWSNGAYAA   RGTNMGNGCN   TGGGTNGGNT
TYWSNGTNCC   NYTNGCNCAY

1801   MGNATHACNG   CNGGNGCNGA   YATHYTNYTN   ATGCCNWSNM
GNTTYGARCC   NTGYGGNYTN

1861 AAYCARYTNT  AYGCNATGGC  NTAYGGNACN  GTNCCNGTNG  TNCAYGCNGT
NGGNGGNYTN

1921   MGNGAYACNG   TNGCNCCNTT   YGAYCCNTTY   AAYGAYACNG
GNYTNGGNTG   GACNTTYGAY

1981   MGNGCNGARG   CNAAYMGNAT   GATHGAYGCN   YTNWSNCAYT
GYYTNACNAC   NTAYMGNAAY

2041   TAYAARGARW   SNTGGMGNGC   NTGYMGNGCN   MGNGGNATGG
CNGARGAYYT   NWSNTGGGAY
```

-continued
Full length clone sequences

```
2101 CAYGCNGCNG  TNYTNTAYGA  RGAYGTNYTN  GTNAARGCNA  ARTAYCARTG
     GTRRGCNAAY

2161     TRRYTNGCNA    CNMGNMGNMG   NWSNTGYMGN   MGNACNTGGA
     CNYTNTTYMG    NMGNYTNTTY

2221     WSNYTNGCNG    CNYTNATGMG   NGCNWSNCAY   YTNMGNMGNG
     CNGAYGGNMG    NMGNTGGYTN

2281     GCNTAYMGNY    TNMGNMGNYT   NMGNGCNYTN   GGNATHTGGG
     CNGGNACNAT    GATGCCNYTN

2341     GGNACNGGNM    GNGGNGTNGT   NTRRTAYGAR   ACNGAYGGNG
```

---

We claim:

1. An isolated nucleic acid molecule comprising a nucleotide sequence encoding a polypeptide having soluble starch synthase activity wherein said polypeptide is encoded by a maize gene, said nucleotide sequence being selected from the group consisting of:

(a) a sequence comprising the nucleotide sequence in SEQ ID NO: 1;

(b) a nucleotide sequence encoding the polypeptide having soluble starch synthase activity which is encoded by the nucleotide sequence in SEQ ID NO: 1;

(c) a nucleotide sequence comprising the nucleotide sequence of the maize cDNA clone contained in the deposit in the National Collection of Industrial and Marine Bacteria Limited with Accession Number 40651;

(d) a nucleotide sequence encoding the polypeptide having soluble starch synthase activity which is encoded by the maize cDNA clone contained in the deposit in the National Collection of Industrial and Marine Bacteria Limited with Accession Number 40651;

(e) a nucleotide sequence encoding the polypeptide having soluble starch synthase activity wherein said polypeptide comprises the amino acid sequence consisting of SEQ ID NO: 33, and, (f) a nucleotide sequence encoding the polypeptide having soluble starch synthase activity wherein said polypeptide comprises the amino acid sequence consisting of SEQ ID NO: 22 and SEQ ID NO: 26.

2. An isolated nucleic acid molecule comprising a nucleotide sequence encoding a polypeptide having soluble starch synthase activity wherein said polypeptide is encoded by a maize gene, said nucleotide sequence being selected from the group consisting of:

(a) a sequence comprising the nucleotide sequence in SEQ ID NO: 2;

(b) a nucleotide sequence encoding the polypeptide having soluble starch synthase activity which is encoded by the nucleotide sequence in SEQ ID NO: 2;

(c) a nucleotide sequence comprising the nucleotide sequence of the maize cDNA clone contained in the deposit in the National Collection of Industrial and Marine Bacteria Limited with Accession Number 40679;

(d) a nucleotide sequence encoding the polypeptide having soluble starch synthase activity which is encoded by the maize cDNA clone contained in the deposit in the National Collection of Industrial and Marine Bacteria Limited with Accession Number 40679; and, (e) a nucleotide sequence encoding the polypeptide having soluble starch synthase activity wherein said polypeptide comprises the amino acid sequence consisting of SEQ ID NO: 32.

3. An isolated nucleic acid molecule comprising a nucleotide sequence encoding a polypeptide having soluble starch synthase activity wherein said polypeptide is encoded by a maize gene, wherein said nucleotide sequence is selected from the group consisting of:

(a) a sequence comprising the nucleotide sequence in SEQ ID NO: 3;

(b) a nucleotide sequence encoding the polypeptide having soluble starch synthase activity which is encoded by the nucleotide sequence in SEQ ID NO: 3;

(c) a nucleotide sequence comprising the nucleotide sequence of the maize cDNA clone contained in the deposit in the National Collection of Industrial and Marine Bacteria Limited with Accession Number 40680;

(d) a nucleotide sequence encoding the polypeptide having soluble starch synthase activity which is encoded by the maize cDNA clone contained in the deposit in the National Collection of Industrial and Marine Bacteria Limited with Accession Number 40680; and, (e) a nucleotide sequence encoding the polypeptide having soluble starch synthase activity wherein said polypeptide comprises the amino acid sequence consisting of SEQ ID NO: 34.

4. An isolated nucleic acid molecule comprising a nucleotide sequence complementary to a nucleotide sequence of claim 1, 2 or 3.

5. A transgenic plant stably transformed with a nucleic acid molecule comprising a nucleic sequence encoding a polypeptide having soluble starch synthase activity wherein said nucleotide sequence is a sequence of claim 1, 2 or 3.

6. A transgenic plant stably transformed with a isolated nucleic acid molecule comprising a nucleotide sequence complementary to a nucleotide sequence of claim 1, 2 or 3.

* * * * *